(12) United States Patent
Bransgrove et al.

(10) Patent No.: US 11,135,590 B2
(45) Date of Patent: Oct. 5, 2021

(54) CASSETTE AND ANALYZER DEVICE

(71) Applicant: Brandon Bransgrove, Gordon (AU)

(72) Inventors: Brandon Bransgrove, Gordon (AU); Steve Hill, Annandale (AU)

(73) Assignee: Brandon Bransgrove, Gordon (AU)

( * ) Notice: Subject to any disclaimer, the term of this patent is extended or adjusted under 35 U.S.C. 154(b) by 267 days.

(21) Appl. No.: 14/429,329

(22) PCT Filed: Nov. 11, 2013

(86) PCT No.: PCT/AU2013/001296
§ 371 (c)(1),
(2) Date: Mar. 18, 2015

(87) PCT Pub. No.: WO2014/043766
PCT Pub. Date: Mar. 27, 2014

(65) Prior Publication Data
US 2015/0202619 A1    Jul. 23, 2015

Related U.S. Application Data

(63) Continuation of application No. PCT/AU2013/001296, filed on Nov. 11, 2013.

(30) Foreign Application Priority Data

May 12, 2013 (AU) ................................ 2013901667

(51) Int. Cl.
*B01L 3/00* (2006.01)
*G01N 33/487* (2006.01)
(Continued)

(52) U.S. Cl.
CPC .............. *B01L 3/508* (2013.01); *A61B 5/157* (2013.01); *G01N 21/78* (2013.01);
(Continued)

(58) Field of Classification Search
CPC ............. B01L 3/508; B01L 2300/0609; G01N 33/48764; G01N 35/00009; G01N 21/78;
(Continued)

(56) References Cited

U.S. PATENT DOCUMENTS 5,096,828 A * 3/1992 Ishizaka ........... G01N 35/00009
356/440
7,961,303 B2 * 6/2011 Sacherer ............ A61B 5/14532
356/39
(Continued)

FOREIGN PATENT DOCUMENTS

EP          2466304 A1    6/2012

OTHER PUBLICATIONS

International Search Report and Written Opinion corresponding to PCT/AU2013/001296 dated Dec. 5, 2013, 6 pages.
(Continued)

*Primary Examiner* — Samuel P Siefke
(74) *Attorney, Agent, or Firm* — Oliff PLC

(57) ABSTRACT

A cassette for loading into a bay of an analyzer device, the cassette having a supply chamber for a test tape, an uptake chamber to receive used tape and a test zone between the chambers, where the tape is positioned at a test site for testing purposes, wherein the cassette includes a frame that extends across the test zone on a loading side of the tape, the frame being in a protective position relative to the tape, parallel to and aligned with the tape in the test zone, to protect the tape as the cassette is inserted into the bay of the analyzer device.

19 Claims, 18 Drawing Sheets

(51) Int. Cl.
*G01N 35/00* (2006.01)
*A61B 5/157* (2006.01)
*G01N 21/78* (2006.01)
*A61B 5/15* (2006.01)

(52) U.S. Cl.
CPC . *G01N 33/48764* (2013.01); *G01N 35/00009* (2013.01); *A61B 5/150022* (2013.01); *A61B 5/150358* (2013.01); *B01L 2300/0609* (2013.01); *G01N 2035/00019* (2013.01)

(58) Field of Classification Search
CPC ............ G01N 2035/00019; G01N 1/10; A61B 5/157; A61B 5/150358; A61B 5/150022; A61B 5/15
See application file for complete search history.

(56) References Cited

U.S. PATENT DOCUMENTS

| | | | | |
|---|---|---|---|---|
| 8,404,478 | B2* | 3/2013 | Harttig | B01L 3/5023 422/424 |
| 2003/0211619 | A1* | 11/2003 | Olson | A61B 5/15146 436/44 |
| 2005/0201897 | A1* | 9/2005 | Zimmer | A61B 10/0045 422/82.05 |
| 2005/0214881 | A1* | 9/2005 | Azarnia | G01N 33/48764 435/7.92 |
| 2005/0232815 | A1* | 10/2005 | Ruhl | G01N 35/00029 422/66 |
| 2007/0065340 | A1* | 3/2007 | Sacherer | G01N 33/48764 422/400 |
| 2008/0049227 | A1 | 2/2008 | Sacherer | |
| 2009/0098644 | A1* | 4/2009 | Sacherer | G01N 33/48764 435/287.7 |
| 2009/0200413 | A1* | 8/2009 | Sacherer | G01N 33/48764 242/538 |
| 2010/0121369 | A1* | 5/2010 | Harttig | A61B 5/1411 606/183 |
| 2011/0263957 | A1* | 10/2011 | Thoes | A61B 5/14532 600/365 |
| 2012/0283528 | A1* | 11/2012 | Konya | A61B 5/02035 600/309 |

OTHER PUBLICATIONS

Nov. 10, 2014 Search Report issued in International Patent Application No. PCT/AU2013/001296.

* cited by examiner

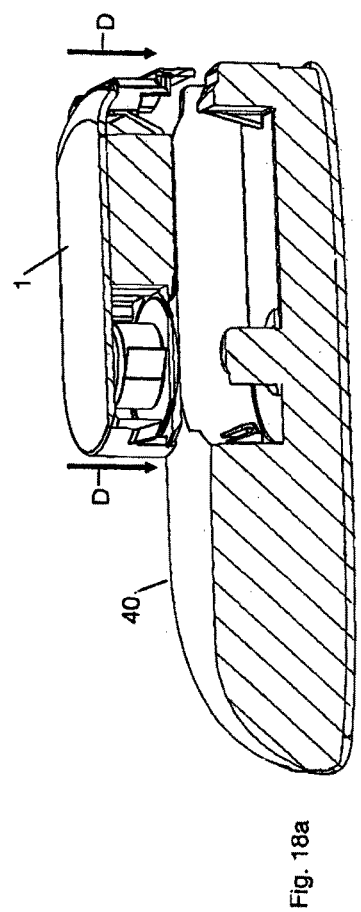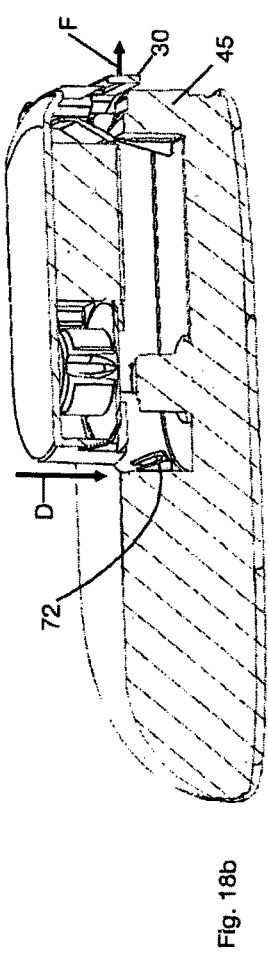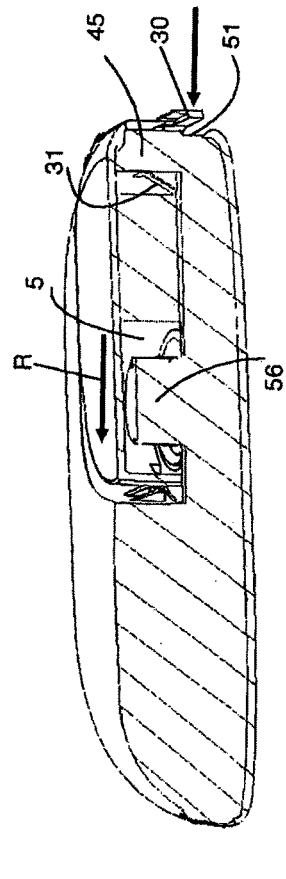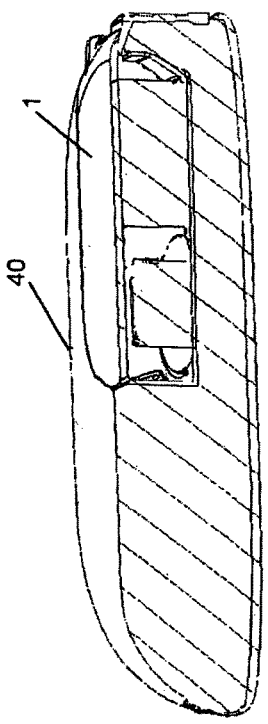

CASSETTE AND ANALYZER DEVICE

RELATED APPLICATIONS

This application claims priority from Australian Patent Application Number 2012904135, Australian Patent Application Number 2012904710 and Australian Patent Application No. 2013901667, the contents of which are incorporated herein by reference.

FIELD OF THE INVENTION

The present invention relates to a cassette for holding a carrier tape with test elements and aspects of loading the cassette into an analyzer device.

BACKGROUND OF THE INVENTION

Body fluid samples such as blood, plasma, urine, interstitial fluid, etc, may be analyzed for various components or properties, such as glucose, cholesterol, pathogens, drugs of abuse, coagulation, hematocrit, etc. The body fluid sample is applied to a test element containing reactive ingredients. A reaction occurs and a result is produced. An instrument may be required to read the result or the result may be interpreted by eye by, for example, colour matching or symbols such as bars, dots, etc.

The test elements may be supplied in multiple numbers along a carrier tape housed in a cassette. The test cassette is provided with two chambers, a sealed supply chamber containing the tape with unused test elements and an uptake chamber for storage of the tape with used test elements. The test cassette can be used in a laboratory analyzer or a portable analyzer.

Loading the cassette into the analyzer can be problematic for a number of reasons. A sensor head of the analyzer is usually required to come into contact with the tape and test element. In the case of biosensors, the sensor head needs to make electrical connection and, in the case of a photometric test, the test element needs to be positioned at a fixed distance from the analyzer optics. As such, the tape needs to be reliably held at a specific test site, relative to the sensor head.

U.S. Pat. No. 7,378,270 (Roobik, et al) discloses a cassette that is inserted into an analyzer, whereupon a sensor head of the analyzer is moved forward into contact with the tape. The moveable head complicates construction and is not ideal for low cost hand held analyzers.

Another solution involves placing the tape over a sensor head manually. This requires the cassette to be manipulated into a position to place the tape onto the sensor head prior to insertion of the cassette into the analyzer. This approach may be suitable for a trained technician but not an unskilled user.

Even when the tape is properly loaded into an analyzer, there may be a problem with a new test element being drawn out of the supply chamber by inadvertent activation of a drive wheel.

If a new test element is inadvertently pulled out of the supply chamber early, the test element will be prematurely exposed to ambient conditions, which may adversely affect the reagents on the test element. For example, the test elements may be exposed to humidity, which can adversely affect the performance of the test.

If a test element is only partially pulled out of the supply chamber, the seal of the supply chamber may be compromised. This can allow moisture to enter the supply chamber. As the test elements are generally hydrophilic, this can damage all the tests in the chamber.

As such, it is desirable to prevent inadvertent activation of the drive wheel unless a test is ready to be undertaken.

OBJECT OF THE INVENTION

The present invention seeks to address or ameliorate at least one of the above problems.

SUMMARY OF THE INVENTION

In accordance with one aspect of the invention, there is provided a cassette for loading into a bay of an analyzer device, the cassette having a supply chamber for a test tape, an uptake chamber to receive used tape and a test zone between the chambers, where the tape is positioned at a test site for testing purposes, wherein the cassette includes a frame that extends across the test zone on a loading side of the tape, the frame being in a protective position relative to the tape, parallel to and aligned with the tape in the test zone, to protect the tape as the cassette is inserted into the bay of the analyzer device.

Preferably, the frame includes guides that direct the tape from the supply chamber to the test zone and away from the test zone to the uptake chamber, and a bridge portion that extends between the guides to protect the tape across the test zone.

Preferably, the cassette includes a biasing element to deflect the cassette into a loaded position when the tape is presented to the test site of the analyzer device, the biasing element causing a housing of the cassette to be displaced in order to move the frame away from the protective position relative to the tape and to leave the tape tensioned across the test site.

Preferably, the biasing element engages with structure of the analyzer, to bias the frame into a receiving recess of the analyzer.

Preferably, the cassette includes at least one catch at a rear end of the cassette remote from the test zone, to lock a rear end of the housing into the bay.

Preferably, the supply chamber includes a supply spool and the uptake chamber includes an uptake spool wherein the supply spool is mounted on a fixed axis internally of the supply chamber and the uptake spool is mounted on a floating axis adapted to slide relative to the housing of the cassette.

In another aspect, there is provided an analyzer device with a bay for receiving the cassette, as described above, and a test site provided on structure that projects into the test zone of the cassette, the structure including a recess, between a floor of the bay and the test site, to receive the frame of the cassette, when the cassette is loaded into the bay.

Preferably, the device includes at least one latch toward an end of the bay, to anchor a rear end of the cassette during a loading operation, when the cassette is moved rearward during insertion into the bay.

Preferably, the structure includes an angled surface against which the biasing element of the cassette engages as the cassette moves into the loaded position to translate the housing rearward, in order to lock the rear of the cassette in the bay and draw the frame into the recess.

Preferably, the structure is in the form of a pillar with a reading head on a front side and a wedge profile on a rear side.

Preferably, the front side and rear side of the pillar are separated by a distance sufficient to energize the biasing element against the rear side and cause the frame to engage with and slide down the front side of the pillar as the cassette is moved into the loaded condition.

In yet another aspect, there is provided an analyzer device and test cassette combination, wherein:

the cassette includes a housing with a supply chamber for holding a tape with test elements, an uptake chamber for storing used tape and a test zone where the tape is presented for testing;

the device includes a bay with a floor and structure with a test site arranged to project into the test zone when the cassette is loaded into the device; the cassette including a frame located between the chambers and adjacent the tape on an insertion side of the tape, to protect the tape as the tape is fitted laterally over the test site; and wherein the cassette is moved in a lengthwise direction during a final stage of loading so as to displace the frame laterally of the test site while the tape remains over the test site.

Preferably, the device includes a capstan that is received in the uptake spool, wherein the capstan is arranged to rotate on a fixed axis and the uptake spool is arranged to rotate on a floating axis so as to be displaced laterally of the housing of the cassette and accommodate relative movement of the capstan, when the cassette is displaced lengthwise during loading.

The device may include a manual or motor drive means of rotating the capstan. Optionally, the device includes a drive wheel coupled to the uptake spool for advancing the tape to the test site and a lock mechanism to selectively prevent the drive wheel engaging and driving the uptake spool. The lock mechanism may also be used with the motor driven version.

Preferably, the device includes a moveable cover over the test site and the lock mechanism is disengaged as a result of the cover being moved to an open position.

Preferably, the lock mechanism includes a lever that is biased into engagement with the drive wheel, to prevent rotation of the drive wheel, and a lug associated with the cover, that moves in response to movement of the cover, to shift the lever into a disengaged position when the cover is opened.

In yet another aspect, there is provided a cassette with a supply chamber that houses a supply spool and an uptake chamber that houses an uptake spool, arranged whereby to hold a tape that passes between the supply spool and the uptake spool, wherein the supply chamber houses the supply spool in a sealed environment and the uptake spool rotates on an a floating axis and is accessible for driving engagement through an opening in a base of the cassette.

Preferably, the floating axis allows the uptake spool to slide laterally inside a housing of the cassette in order to accommodate relative movement of a capstan that is used to drive the uptake spool.

BRIEF DESCRIPTION OF THE DRAWINGS

The invention is more fully described, by way of a non-limiting example only, with reference to the accompanying drawings, in which:

FIG. 18 illustrates insertion of the cassette into the analyzer device.

DETAILED DESCRIPTION OF THE INVENTION

Figure 1:
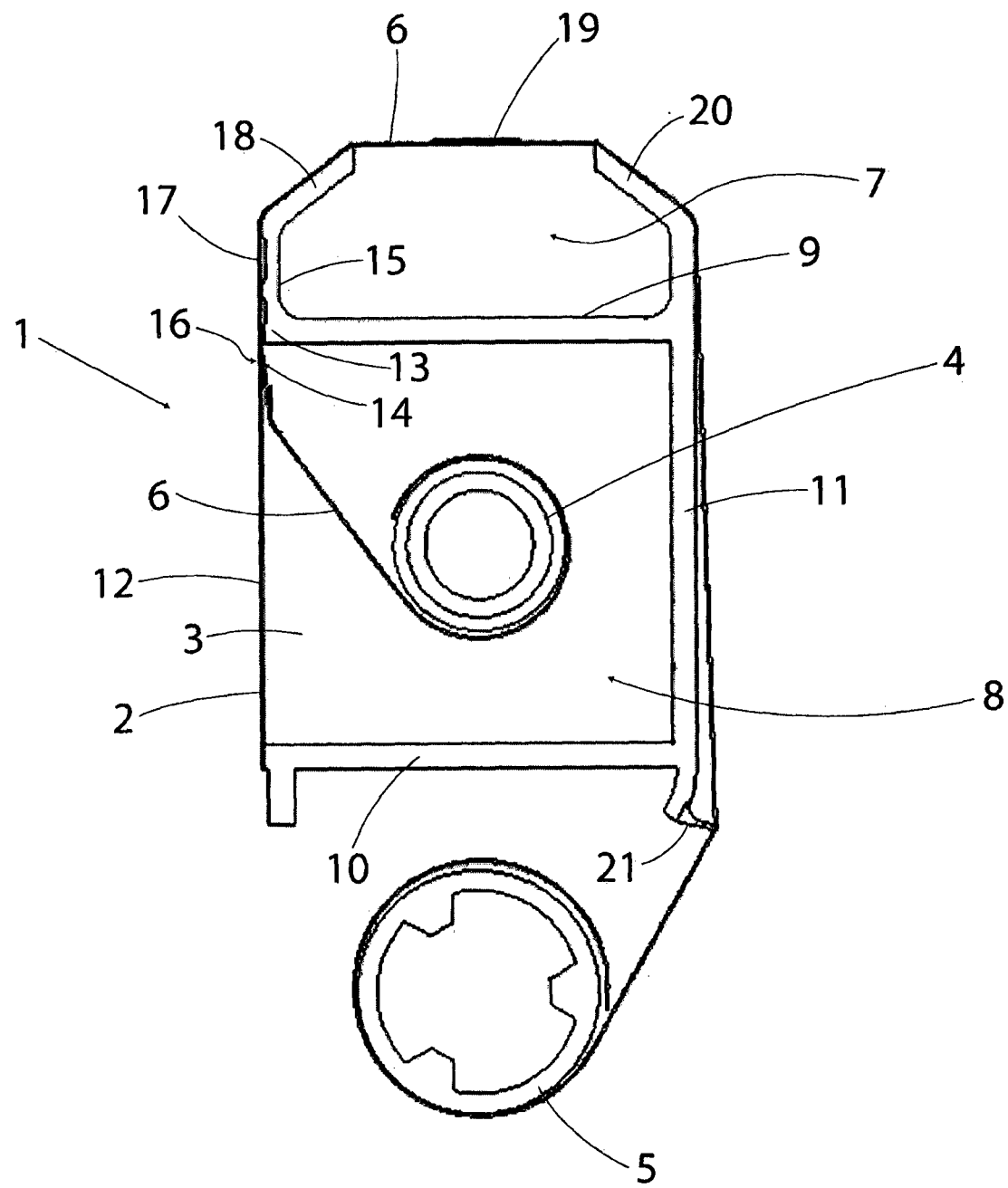
FIG. 1 is a top view of a cassette shell.

Referring firstly to FIG. 1, part of a cassette 1 is shown in the form of a shell 2 that includes a body 3 with a supply spool 4 and a uptake spool 5. A tape 6 extends from the supply spool 4, through a test zone 7 and onto the uptake spool 5.

The supply spool 4 is located in a supply chamber 8 that is defined by a front wall 9, a back wall 10 and a side wall 11. A further side wall 12 serves to close the chamber 8. The wall 12 is secured to the back wall 10 and projects past an end 13 of the front wall 9 so as to define a small gap 14 between the wall 12 and the front wall 9, for the tape 6 to exit the chamber 8.

An elongate finger 15 projects from the front wall 9 and the Wall 12 is arranged to sit in close proximity to the finger 15 to maintain a seal 16 against the tape 6, as the tape 6 is drawn through a channel 17 between the wall 12 and finger 15. The finger 15 terminates in a guide 18 that is angled toward the test zone 7, to direct the tape 6 to the test zone 7, where a test element 19 is located for testing.

A corresponding guide 20 is positioned on an opposite side of the test zone 7 for directing used tape 6 back down the side wall 11, over a brake 21 (that keeps the tape in tension across the test zone 7) and onto the uptake spool 5.

Figure 2:
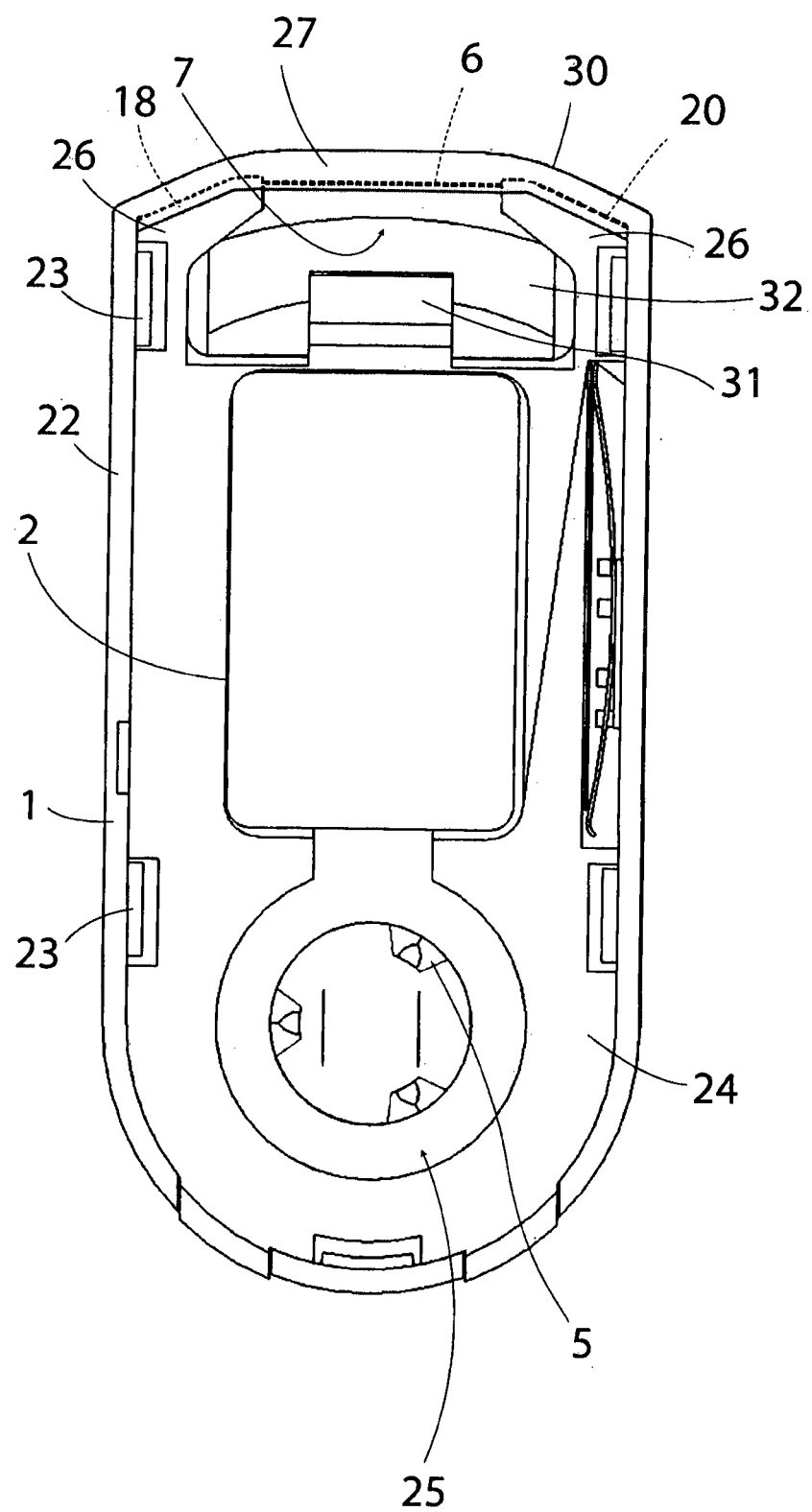
FIG. 2 is a bottom view of a cassette.

Referring to FIG. 2, the cassette shell 2 is shown fitted into a housing 22 to form the completed cassette 1. The housing 22 is snap-fitted onto the shell 2 using clips 23 so that a base 24 of the housing 22 at least partially closes over the uptake spool 5 and a circular opening 25 is provided to allow access to the spool 5.

The base 24 includes side extensions 26 that overlay the guides 18, 20. A bridge portion 27 extends between the guides 18, 20 to form a frame 30 that aligns with the tape 6, shown in dashed lines. A biasing element 31 projects from the base 24 into a free space 32 adjacent the test zone 7.

Figure 3:
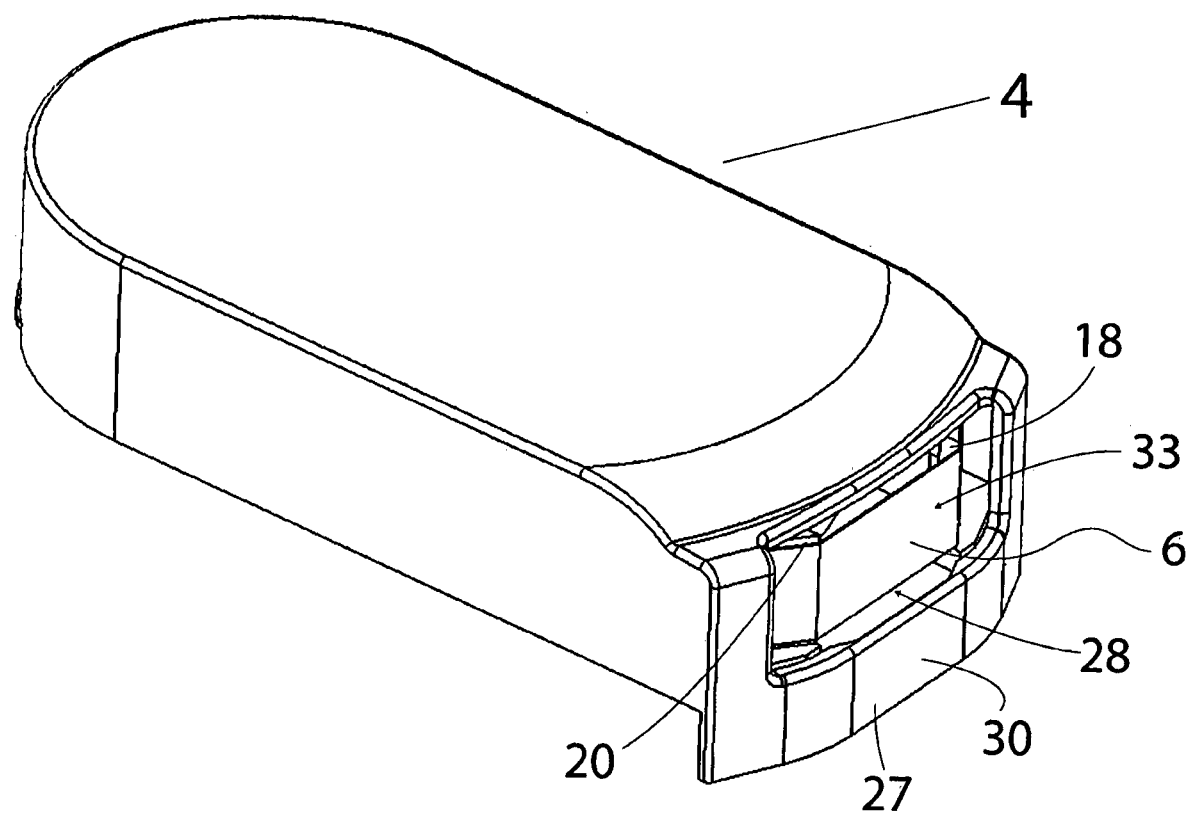
FIG. 3 is a perspective view of a front of the cassette.

Referring now to FIG. 3, the tape 6 is illustrated as being tensioned between the guides 18, 20, parallel to and laterally adjacent the frame 30 so that the bridge portion 27 is in a protective position relative to the tape 6. The frame 30 thereby protects the tape 6 laterally, on a loading side 28, from damage or kinking. The frame 30 is shown as forming a window 33 in front of the tape 6, so that blood or other material for testing can be deposited on the tape 6.

Figure 4:
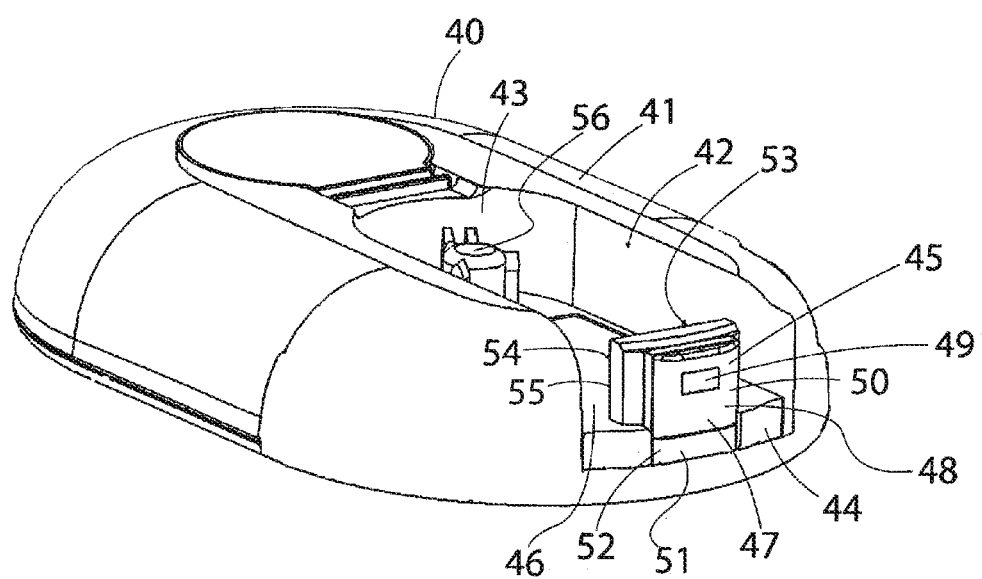
FIG. 4 is a perspective view of a back of an analyzer device.

Referring now to FIG. 4, an analyzer device 40 is illustrated as including a main body 41 with a recessed bay 42 with a curved inner end 43 and an open outer end 44. Structure 45 projects upwardly from a floor 46 of the bay 42, adjacent the outer end 44 of the bay 42. The structure 45 includes a post 47 with a sensor head 48 that defines a test site 49 on a front side 50 and a recess 51 at a lower end 52 of the post 47. An angled surface 53 is provided in the form of a wedge profile 54 on a rear 55 of the structure 45.

Figure 5:
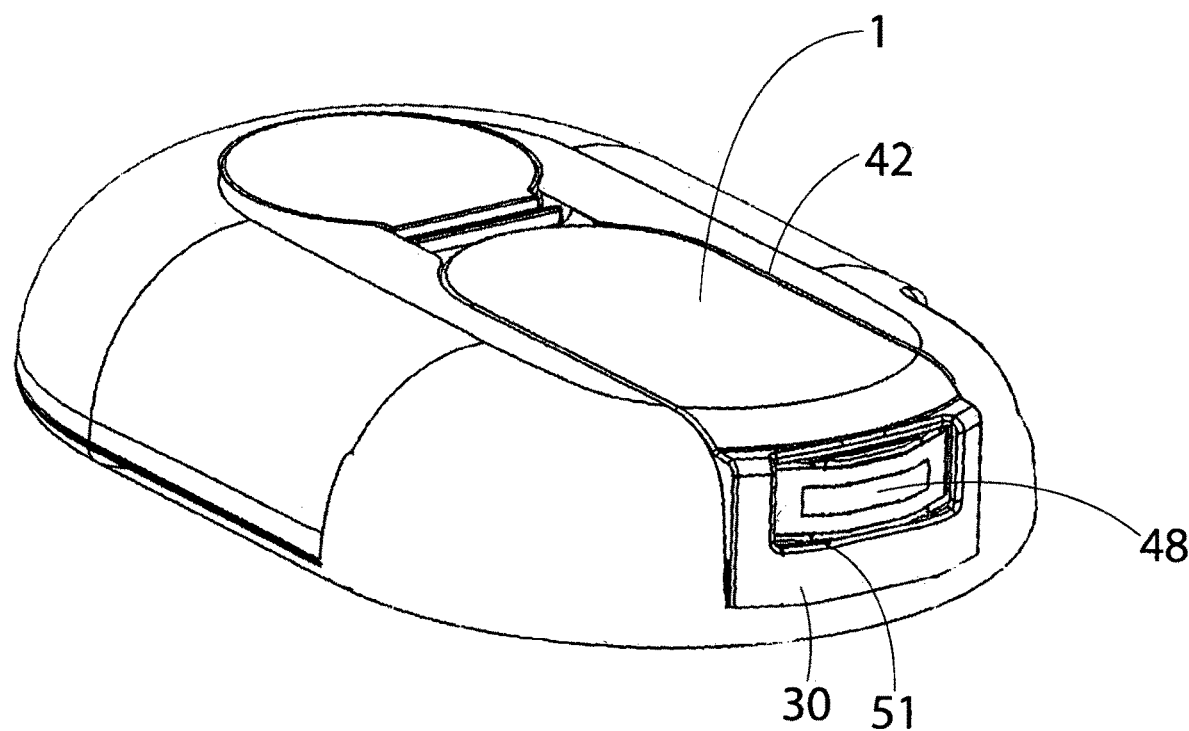
FIG. 5 is a perspective view of a cassette loaded into the device.

A capstan 56 projects up from the floor 46, toward the inner end 43 of the bay 42. The capstan 56 is designed to fit in the uptake spool 5 and the structure 45 is designed to be received in the test zone 7 of the cassette 1, when the cassette 1 is loaded in the bay 42 of the device 40, as shown in FIG. 5, where the frame 30 is shown clipped down over the sensor head 48 and into the recess 51, to lock the cassette 1 in place.

Figure 6:
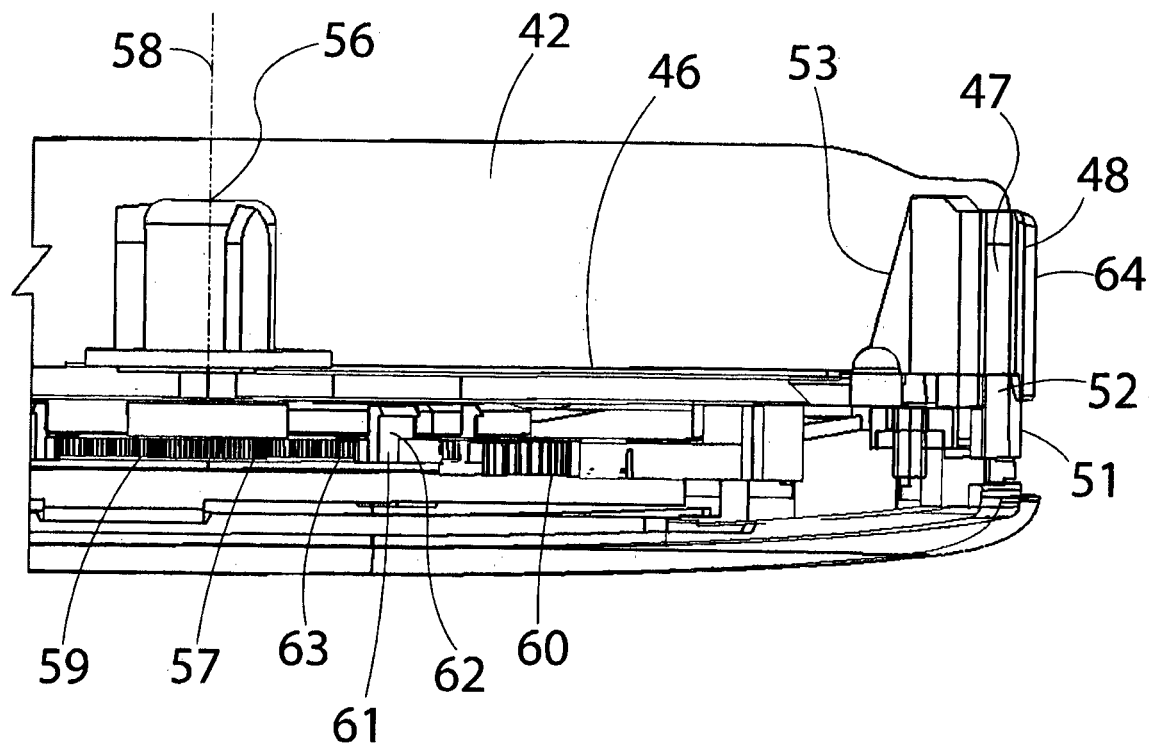
FIG. 6 is a partial cross-sectional view of the cassette and device.

With reference to FIG. 6, the capstan 56 is shown connected to a gear mechanism 57 to rotate around a fixed axis 58. The gear mechanism 57 includes a drive wheel 59 and an input gear 60. A lock mechanism 61 that includes a lever 62 is provided to engage teeth 63 of the drive wheel 59 and thereby prevent rotation of the drive wheel 59.

FIG. 6 also clearly shows the angled surface 53, behind the sensor head 48, as being wedge shaped and tapered rearward, toward the floor 46 of the bay 42. The recess 51 at the lower end 52 of the post 47 is defined underneath a forward nose portion 64 of the post 47.

Figure 7:
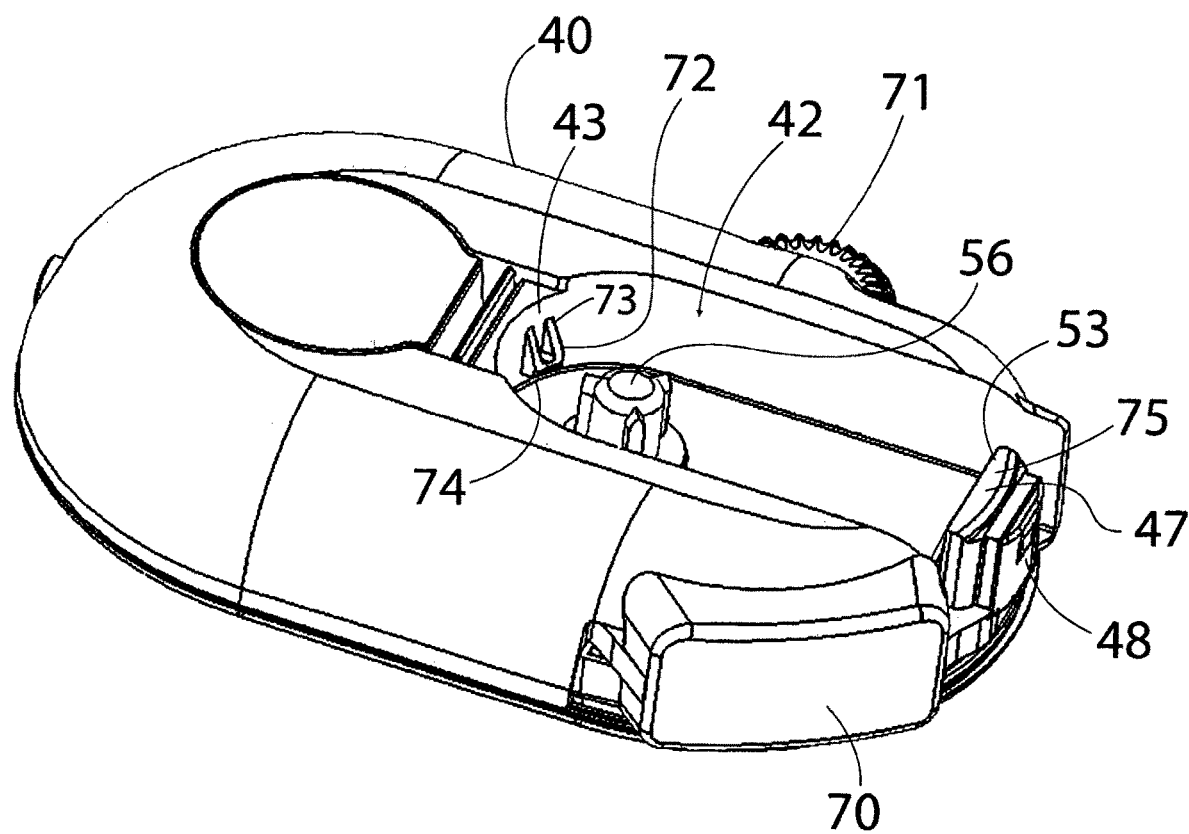
FIG. 7 is an elevated perspective view of the back of the device.
Figure 8:
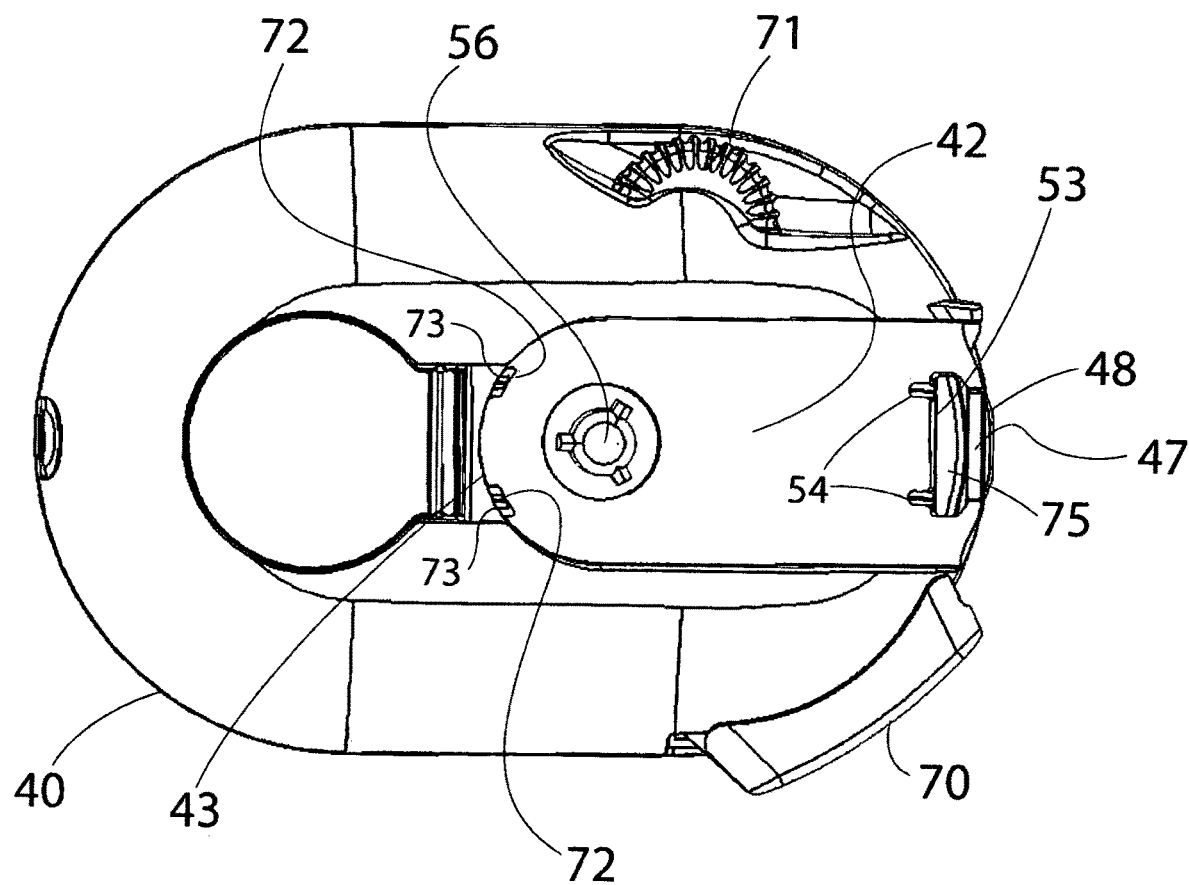
FIG. 8 is a plan view of the back of the device.

Referring to FIGS. 7 and 8, the device 40 also includes a slide cover 70, shown in the open position, where the sensor head 48 is exposed for testing purposes. In that arrangement, the lock mechanism 61 (as shown in FIG. 6) is disengaged to allow the capstan 56 to be rotated under action of a thumb wheel 71.

The bay 42 also includes two latches 72 at the inner end 43 of the bay 42, adjacent the floor 46. The latches 72 have a sloped upper deck 73 and an undercut ledge 74. The angled surface 53 is provided from a top surface 75 of the post 47 and continues down onto spaced apart wedge profiles 54 that are substantially in alignment with the latches 72 at the inner end 43 of the bay 42.

Figure 9:
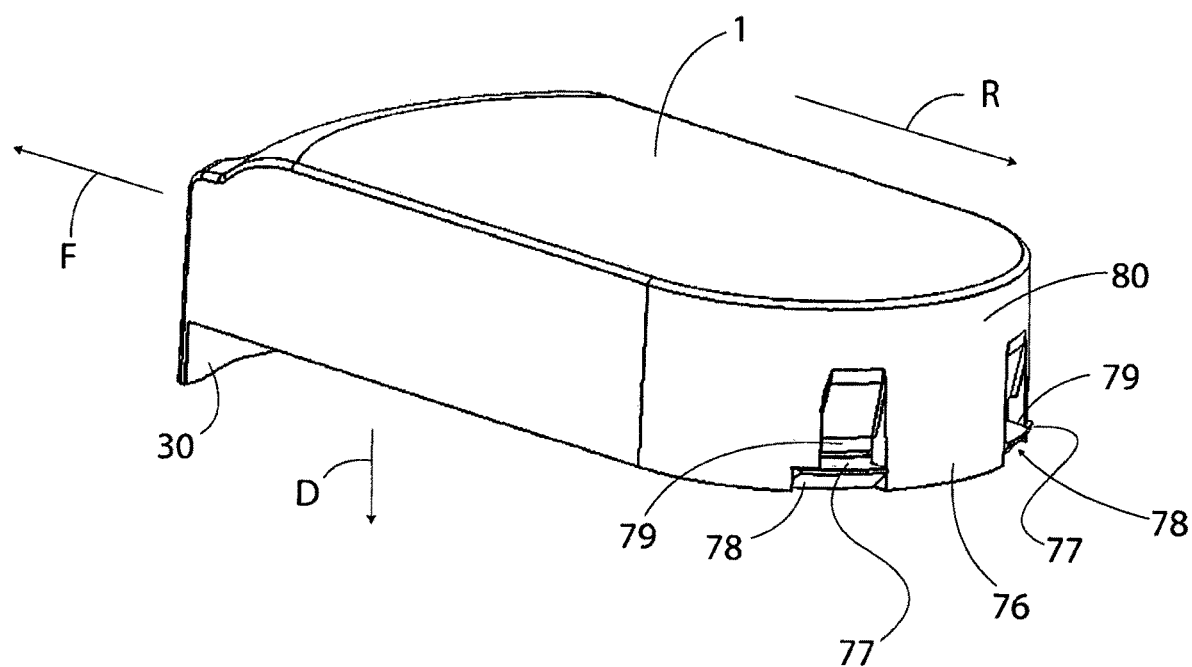
FIG. 9 is a perspective view of a rear of the cassette.

Turning now to FIG. 9, a rear lower edge 76 of the cassette 1 is provided with two catches 77 that are each formed with a bevelled edge 78 and an upper ledge 79. During movement of the cassette 1 into the device 40 of FIG. 7, in an insertion direction indicated by arrow "D", the bevelled edge 78 of each catch 77 is designed to engage with the sloped upper deck 73 of the latches 72. This has the effect of forcing the cassette 1 in an initial forward direction "F" to ensure the frame 30 clears the structure 45 at the outer end 44 of the bay 42, whilst protecting the tape 6 from lateral engagement or damage from the structure 45.

After the bevelled edges 78 clear the respective upper decks 73, the upper ledges 79 slide under the undercut ledges 74, in a rearward direction "R", to lock a rear end 80 of the cassette 1 into the device 40.

Figure 10:
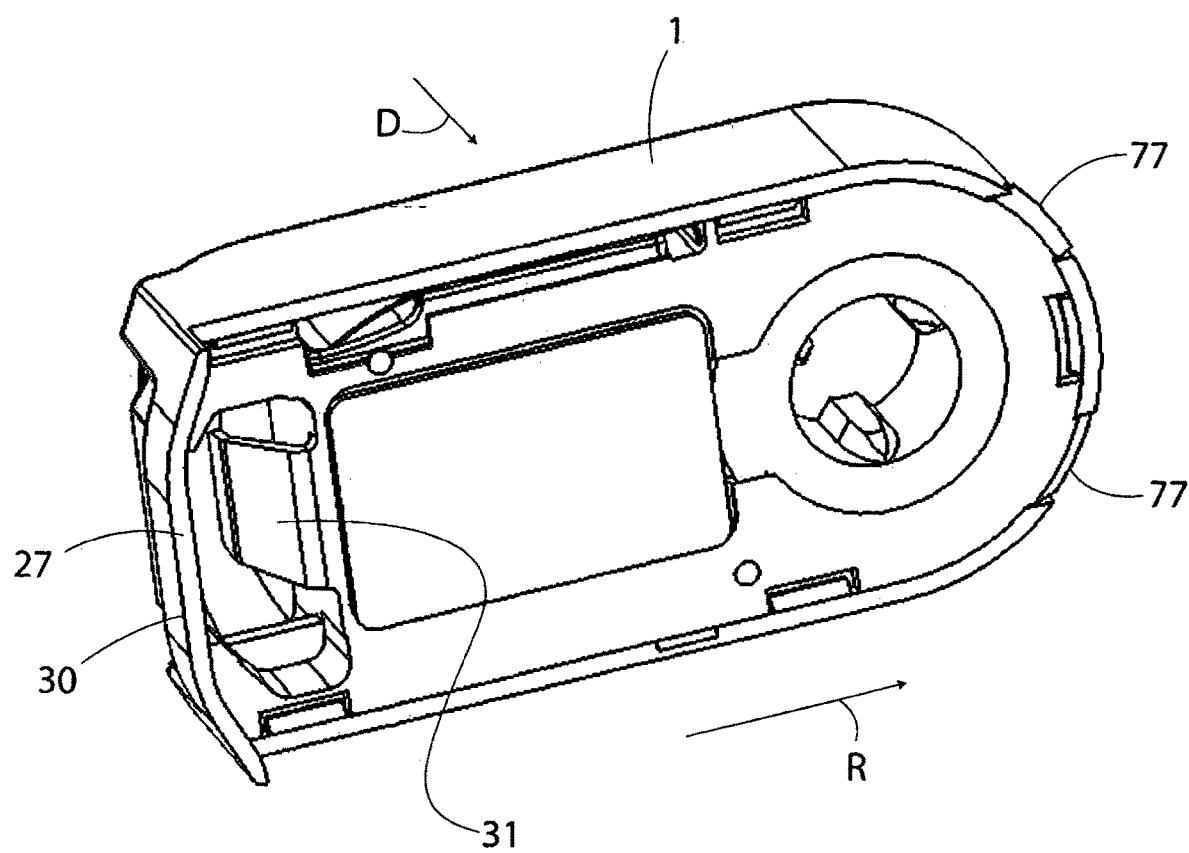
FIG. 10 is a bottom perspective view of the cassette.

Referring to FIG. 10, the biasing element 31 is positioned to abut the wedge profile 54 at the rear 55 of the structure 45 (as shown in FIG. 8), when the frame 30 extends over the sensor head 48. As the cassette 1 is moved in the insertion direction "D", the frame 30 is forced down over the structure 45 which energizes the biasing element 31 and causes the frame to resiliently engage the post 47, until the bridge portion 27 is biased into the recess 51 on the post 47, which then allows the cassette 1 to be urged in the rearward direction "R" to thereby lock the catches 77 under the latches 72. This action causes the tape 6 to be tensioned across the test site 49, over the sensor head 48. As may be appreciated, during movement of the cassette 1 in the insertion direction "D", the tape 6 is protected from sideward engagement with the sensor head 48 by the frame 30, which prevents damage to the tape 6.

The entire process of loading the cassette 1 into the device 40 is illustrated in the schematic drawings of FIG. 18.

In particular, FIG. 18a shows the cassette 1 being moved in the insertion direction "D". FIG. 18b illustrates the frame 30 being urged in the forward direction "F", as movement of the cassette continues in the direction "D". Forward movement of the frame 30 is effected by a combination of the resilient engagement with the structure 45 and the cassette 1 engaging the latches 72.

In FIG. 18c, the capstan 56 has been received in the uptake spool 5 and the action of the biasing element 31 on the structure 45 urges the cassette 1 in the rearward direction "R", such that the frame 30 is snapped into the recess 51. FIG. 18d shows the cassette 1 in the fully loaded condition.

Figure 11:
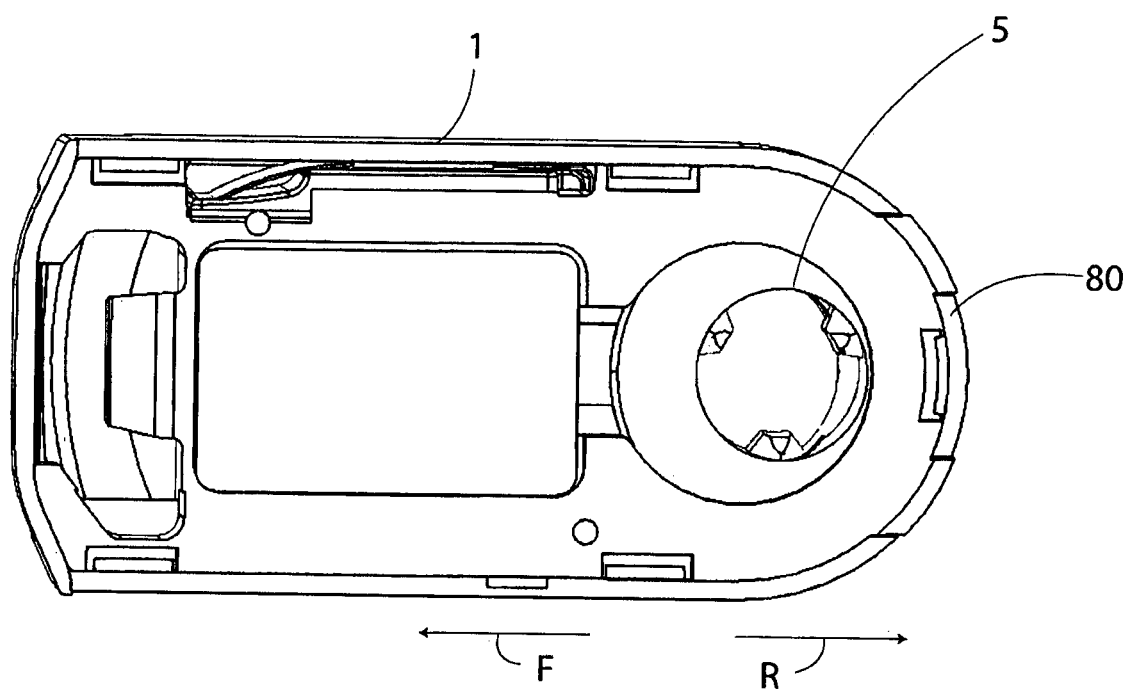
FIG. 11 is a bottom view of the cassette, illustrating displacement of a take-up spool.

Referring now to FIG. 11, the relative position of the uptake spool 5 within the cassette during the loading operation is described in more detail. The uptake spool 5 is shown laterally displaced toward the rear end 80 of the cassette 1. This is the position the spool 5 needs to adopt to engage the capstan 56 during the initial insertion of the cassette 1 into the bay 42 of the device 40. Since the capstan 56 is arranged to rotate on a fixed axis 58, the uptake spool 5 needs to be able to float relative to the capstan 56, as the cassette housing 22 moves relative to the capstan 56 during insertion. In particular, the cassette 1 initially slides in the forward direction "F" and then back in the rearward direction "R" during insertion into the device 40.

Figure 12:
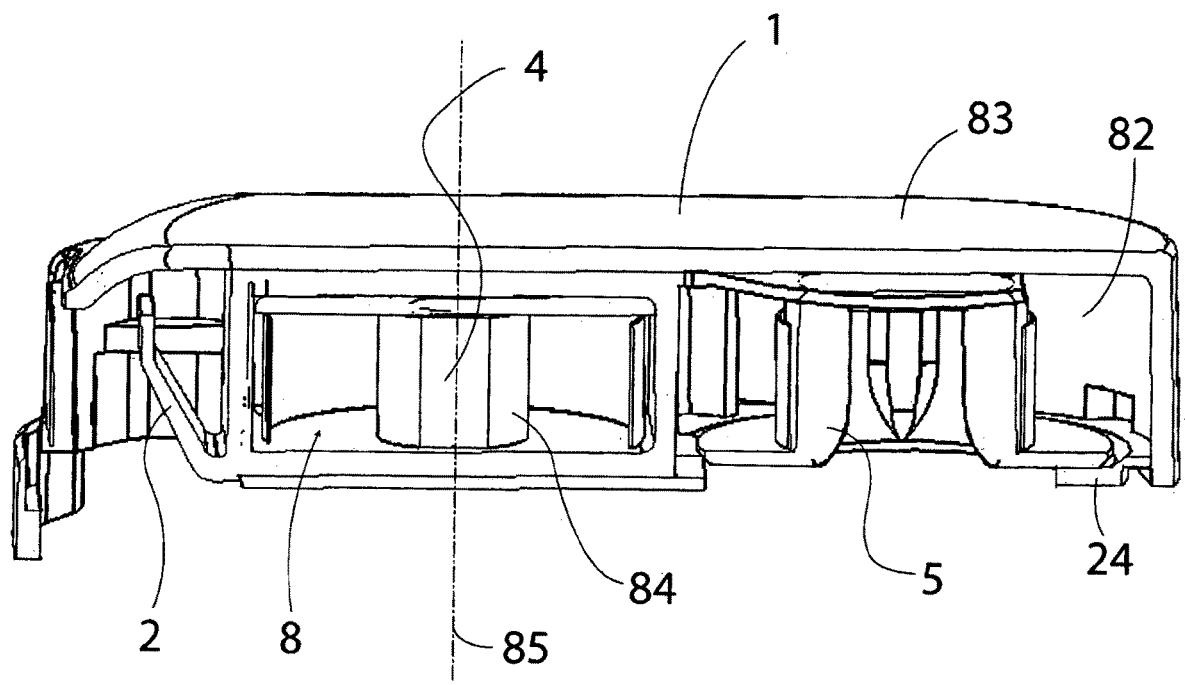
FIG. 12 is a perspective cross-sectional view of the cassette.

With regard to FIG. 12, the uptake spool 5 is allowed to float by simply being housed in an uptake chamber 82, which is defined between the base 24 and a lid 83 of the cassette 1. As such, the uptake spool 5 is free to float by sliding lengthwise of the uptake chamber 82 and cassette 1, as needed. The supply spool 4, on the other hand, is mounted on a hub 84 that is sealed within the supply chamber 8, to rotate on a fixed axis 85.

Since the uptake spool 5 is free to move lengthwise of the housing 22, the spool 5 does not present a reliable mechanism for maintaining tension on the tape 6 when the cassette 1 is out of the analyzer device 40. As such, a separate and independent mechanism is used to maintain tension on the tape 6, in the form of the brake 21, described with reference to FIG. 1. The brake 21 is preferably an integrally moulded part of the housing 22, positioned between the test zone 7 and the uptake spool 5. The brake 21 is formed of thermoplastic elastic material, to grip the tape against the housing 22 and maintain tension of the tape 6 across the test zone 7, thereby allowing the spool to move freely when our of the analyzer 40.

Figure 13:
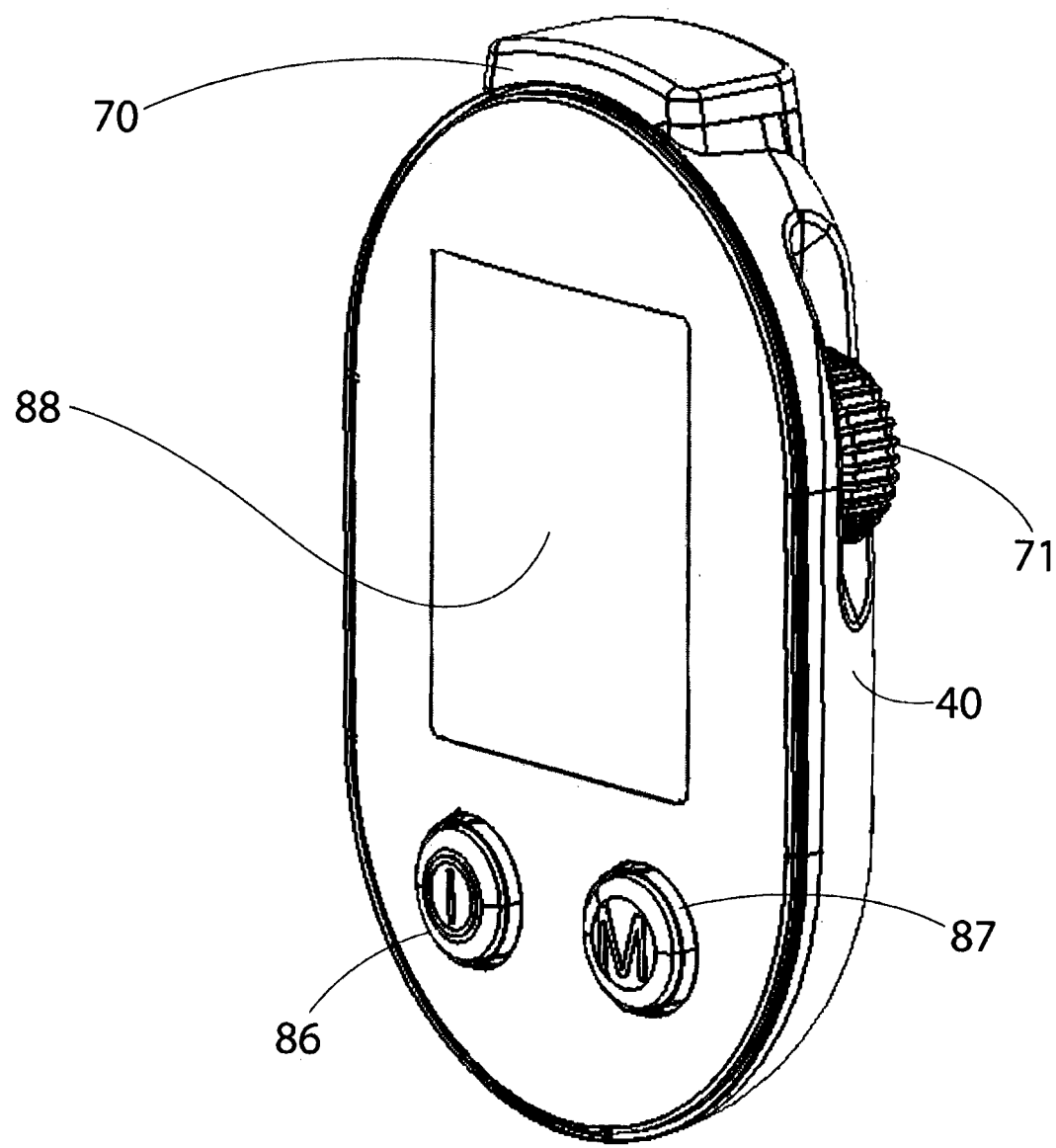
FIG. 13 is a front view of the device.

Referring to FIG. 13, the device 40 has a power button 86, a test function button 87 and a screen 88 for displaying a test result. The device 40 is shown with the slide cover 70 in a closed position, which locks the thumb wheel 71 against rotation, or at least prevents the tape 6 from being wound forward by the wheel 71, even in the event the wheel is turned.

Figure 14:
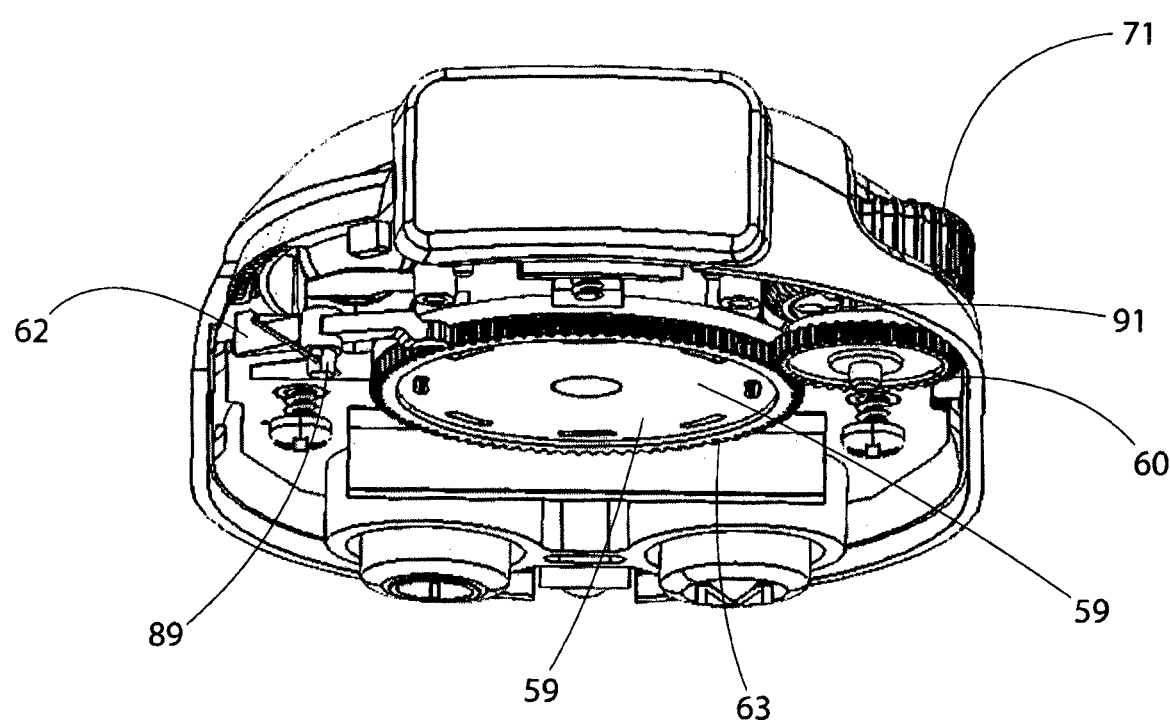
FIG. 14 is a top front perspective view of the device, without a cover plate, illustrating an interior of the device.

Referring to FIG. 14, the thumb wheel 71 is shown connected to the input gear 60, which meshes with the teeth 63 of the drive wheel 59. The lever 62 is mounted on a boss 89 and a resilient member 90 holds the lever in engagement with the drive wheel 59. The thumb wheel 71 is thereby prevented from rotating the drive wheel 59. A clutch device 91 may be provided to allow free rotation of the thumb wheel 71 until the lever 62 is released.

Figure 15:
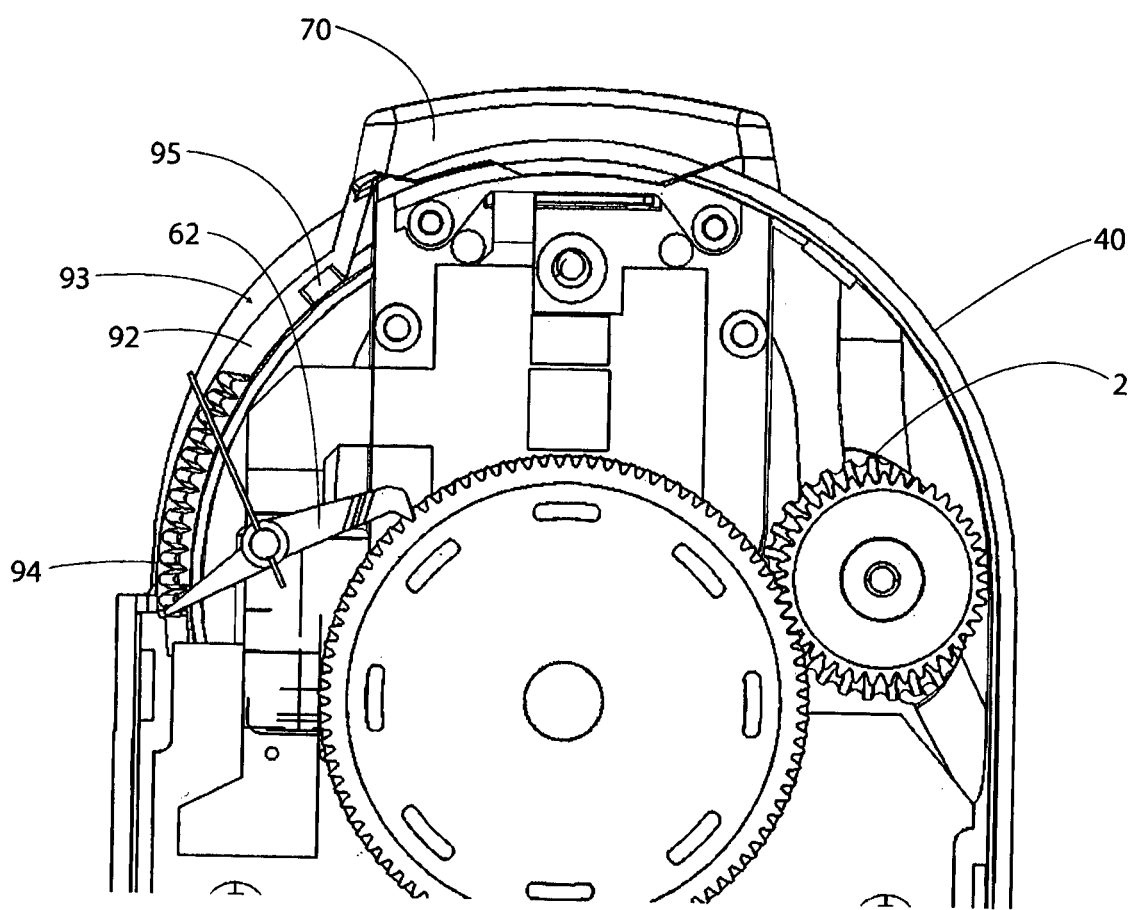
FIG. 15 is a front view of the interior of the device.

Referring now to FIG. 15, the slide cover 70 is attached to a tail 92 that is constrained to slide along an elongated track 93 in a side 94 of the device 40. The tail 92 has a lug 95 arranged to engage the lever 62 when the slide cover 70 is opened.

Figure 16:
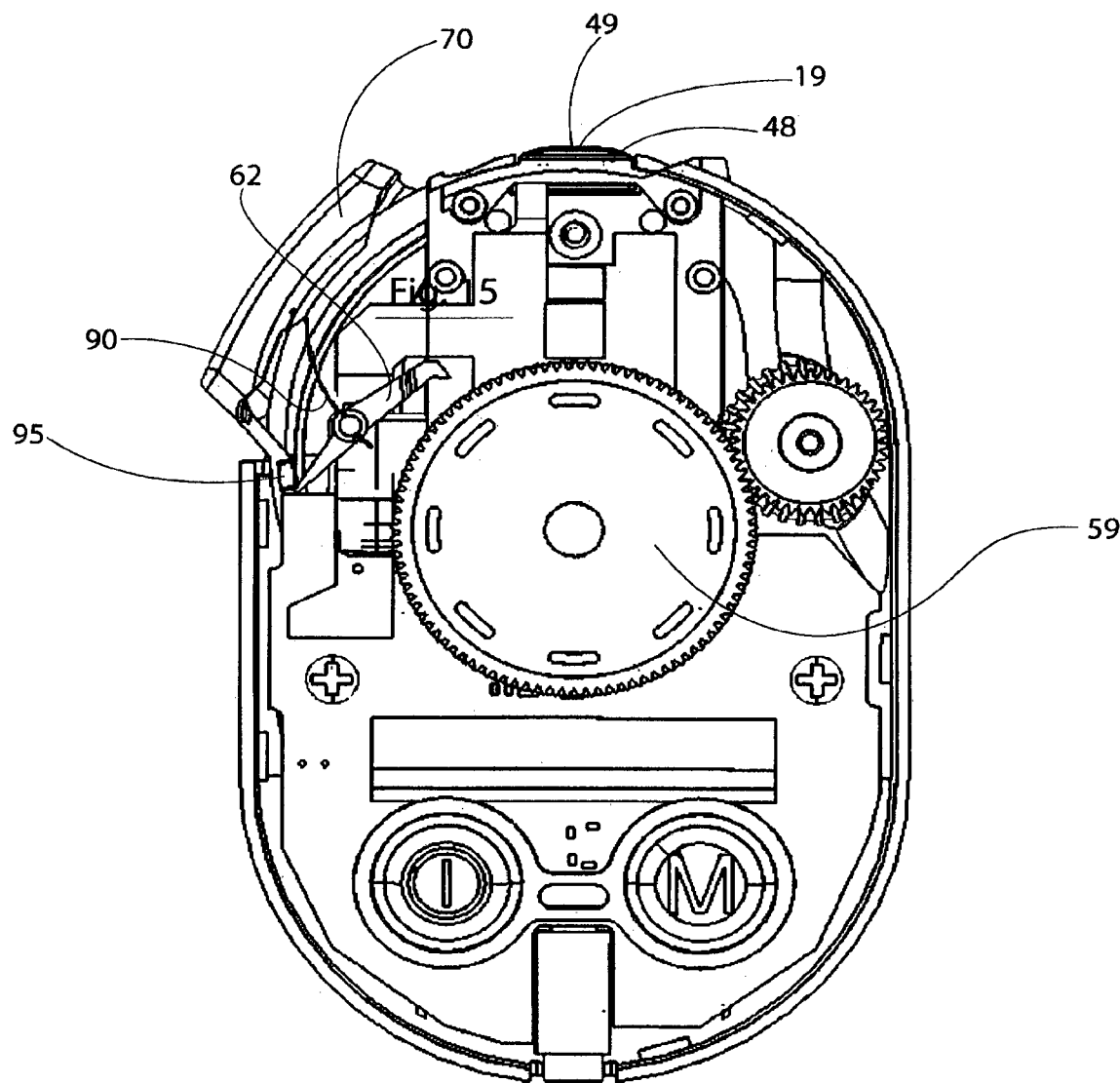
FIG. 16 is a front view of the interior of the device, illustrating a lock mechanism in a release condition.

With reference to FIG. 16, the slide cover 70 is shown in an open position, where the lug 95 has engaged the lever 62 and pivoted the lever 62 against the resistance of the resilient member 90, to allow rotation of the drive wheel 59. In that position, the thumb wheel 71 can be rotated to advance the tape 6 across the sensor head 48 to present a new test element 19 to the test site 49.

Figure 17:
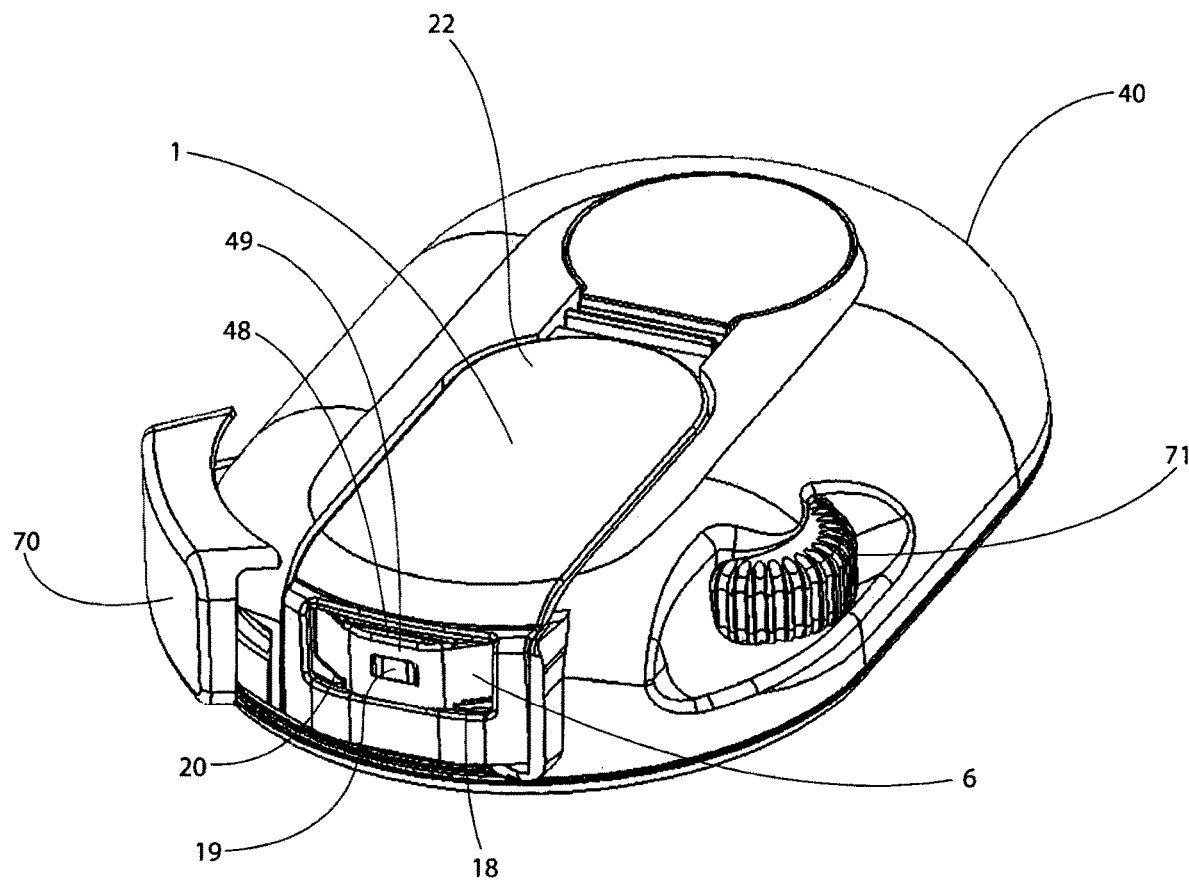
FIG. 17 is a top perspective view of the device of FIG. 16, with the lock mechanism in the release condition.

With regard to FIG. 17, the slide cover 70 is again shown in an open position in which the tape 6 is shown tensioned between the guides 18, 20 so that the test element 19 is located over the sensor head 48. This allows a sample of blood or other material to be deposited on the test element 19 for testing purposes. When the test has been completed, the tape 6 can be advanced by rotating the thumb wheel 71, which engages the drive wheel 59 to wind the used test element 19 into the uptake chamber 82 and index a fresh test element 19 out of the supply chamber 8 and onto the test site 49.

If testing is complete, the cover 70 can be slid back into the closed position, to engage the lock mechanism 61 in order to secure the drive wheel 59 from further rotation. As such, the tape 6 is prevented from being inadvertently drawn out of the supply chamber 8.

It should be appreciated from the above that the cassette 1 allows the tape 6 to be reliably fixed over a test site 49, without damage from lateral loading over the sensor head 48. Since the cassette 1 is displaced longitudinally and rearward during insertion, the tape 6 is tensioned over the test site 49 such as to provide close proximity and contact between the tape 6 and the sensor head 48, if needed. To remove the cassette 1, the housing 22 is simply pressed in a forward direction, against the resistance of biasing element 31, which causes the cassette 1 to lift upwardly on the angled surface 53 of the structure 45 and away from the floor 46 of the bay 42. As such, the cassette 1 may be easily and reliably swapped in and out of the device 40. By using the cassette 1, the tape 6 is automatically loaded onto the sensor head 48, without requiring a skilled technician to separately load the tape onto the test site 49.

LIST OF PARTS

1. Cassette
2. Shell
3. Body
4. Supply spool
5. Uptake spool
6. Tape
7. Test zone
8. Supply chamber
9. Front wall
10. Back wall
11. Side wall
12. Side wall
13. End
14. Gap
15. Finger
16. Seal
17. Channel
18. Guide
19. Test element
20. Guide
21. Spacer
22. Housing
23. Clips
24. Base
25. Opening
26. Side extensions
27. Bridge portion
28. Loading side
30. Frame
31. Biasing element
32. Space
33. Window
40. Analyzer device
41. Body
42. Bay
43. Inner end
44. Outer end
45. Structure
46. Floor
47. Post
48. Sensor head
49. Test site
50. Front side
51. Recess
52. Lower end
53. Angled surface
54. Wedge profile
55. Rear
56. Capstan
57. Gear mechanism
58. Fixed axis
59. Drive wheel
60. Input gear
61. Lock mechanism
62. Lever
63. Teeth
70. Cover
71. Wheel
72. Latch
73. Upper deck
74. Ledge
75. Surface
76. Lower edge
77. Catch
78. Bevelled edge
79. Upper ledge
80. Rear end
82. Uptake chamber
83. Lid
84. Hub
85. Fixed axis
86. Power button
87. Test button
88. Screen
89. Boss
90. Resilient member
91. Clutch device
92. Tail
93. Track
94. Side
95. Lug

The invention claimed is:

1. A cassette for loading into a bay of an analyzer device, the cassette comprising:
a housing;

a supply chamber within the housing and containing a supply spool of test tape;

an uptake chamber within the housing and configured to receive the test tape after the test tape has been tested;

an opening on the cassette, the test tape extending through the opening so as to be tested by a sensor head of the analyzer device in the opening when the cassette is loaded in the bay of the analyzer device;

a frame attached to the housing and that extends parallel to at least a portion of the test tape in the opening, the frame being laterally offset from the test tape in the opening and disposed farther away from the supply chamber than the test tape in the opening so that the frame is configured to protect the test tape as the cassette is loaded into the bay; and a spring attached to the cassette, the spring being configured to engage the sensor head to bias the housing when the cassette is loaded into the bay such that the frame moves into a ledge on the sensor head.

2. The cassette of claim 1, further comprising:

guides that direct the test tape from the supply chamber to the opening and away from the opening to the uptake chamber; and a bridge portion on the frame, the bridge portion being laterally offset from the guides, disposed farther away from the supply chamber than the guides, and partially defining the opening.

3. The cassette of claim 1, wherein the cassette includes a catch at an opposite end of the housing from the opening to lock the housing into the bay.

4. The cassette of claim 1, further comprising:

an uptake spool in the uptake chamber, the uptake spool receiving the test tape after the test tape has been tested by rotating about a winding axis of the uptake spool, the uptake spool being movably mounted to move in a direction perpendicular to the winding axis of the uptake spool, wherein the supply spool is mounted on a fixed axis in the supply chamber.

5. The cassette of claim 4, further comprising:

a brake to grip the test tape against the housing and maintain tension in the test tape across the opening, while allowing the uptake spool to slide relative to the housing.

6. The cassette of claim 5, wherein the brake is formed integrally with the housing from a thermoplastic elastic material to grip the test tape between the opening and the uptake spool.

7. The cassette of claim 1, wherein the spring projects from the housing into a free space adjacent the opening.

8. The cassette of claim 1, wherein the frame extends downward from the housing.

9. The cassette of claim 1, wherein the frame extends from one side of the housing to an opposite side of the housing.

10. The cassette of claim 1, wherein the spring is located behind the opening and forward of the supply chamber and the uptake chamber.

11. An analyzer device comprising:

a body with the bay located therein;

the sensor head; and the cassette of claim 1 loaded in the bay, wherein the sensor head projects behind and contacts the test tape in the opening.

12. The analyzer device of claim 11, further comprising:

a latch in the bay, the latch engaging a catch of the cassette.

13. The analyzer device of claim 11, wherein the sensor head includes an angled surface against which of the cassette engages to translate the housing as the cassette moves into a loaded position, in order to lock the housing in the bay and draw the frame into the ledge.

14. The analyzer device of claim 13, wherein the sensor head has a reading head on a first side and a wedge profile on a second side opposite the first side.

15. The analyzer device of claim 14, wherein the first and second sides of the sensor head are separated by a distance sufficient to energize the spring against the second side and cause the frame to engage with and slide down the first side of the sensor head as the cassette is moved into a loaded position.

16. The analyzer device of claim 11, further comprising:

a drive wheel for advancing the test tape in the cassette to the opening and a lock mechanism to selectively prevent the drive wheel from driving the test tape.

17. The analyzer device of claim 16, further comprising:

a moveable cover over the opening, wherein the lock mechanism is disengaged as a result of the moveable cover being moved to an open position.

18. The analyzer device of claim 17, wherein the lock mechanism includes:

a lever that is biased into engagement with the drive wheel to prevent rotation of the drive wheel, and a trigger associated with the moveable cover that moves in response to movement of the moveable cover to shift the lever into a disengaged position when the moveable cover is opened.

19. The analyzer device of claim 11, wherein the sensor head is fixed relative to the body of the analyzer device.

* * * * *

UNITED STATES PATENT AND TRADEMARK OFFICE
CERTIFICATE OF CORRECTION

PATENT NO. : 11,135,590 B2
APPLICATION NO. : 14/429329
DATED : October 5, 2021
INVENTOR(S) : Brandon Bransgrove et al.

Page 1 of 1

It is certified that error appears in the above-identified patent and that said Letters Patent is hereby corrected as shown below:

On the Title Page

Item (30) Foreign Application Priority Data:
"May 12, 2013  (AU)………………………2013901667"

Should be:
-- May 12, 2013        (AU)……………………… 2013901667
September 22, 2012     (AU)……………………… 2012904135
October 29, 2012       (AU)……………………… 2012904710 --

Signed and Sealed this
Twenty-fifth Day of January, 2022

Drew Hirshfeld
*Performing the Functions and Duties of the*
*Under Secretary of Commerce for Intellectual Property and*
*Director of the United States Patent and Trademark Office*